United States Patent
Cambier et al.

(10) Patent No.: US 6,532,298 B1
(45) Date of Patent: *Mar. 11, 2003

(54) PORTABLE AUTHENTICATION DEVICE AND METHOD USING IRIS PATTERNS

(75) Inventors: James L. Cambier, Medford, NJ (US); John E. Siedlarz, Indian Mills, NJ (US)

(73) Assignee: Iridian Technologies, Inc., Moorestown, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 09/396,083

(22) Filed: Sep. 14, 1999

Related U.S. Application Data

(63) Continuation-in-part of application No. 09/310,302, filed on May 12, 1999, which is a continuation-in-part of application No. 09/199,369, filed on Nov. 25, 1998, now Pat. No. 6,377,699.

(51) Int. Cl.⁷ .............................................. G06K 9/00
(52) U.S. Cl. ....................................... 382/117; 340/5.82
(58) Field of Search ................................ 382/110, 117, 382/115, 116; 351/206, 218, 209; 340/5.2, 5.52, 5.53, 5.81–5.83

(56) References Cited

U.S. PATENT DOCUMENTS

| | | | |
|---|---|---|---|
| 4,109,237 A | 8/1978 | Hill | 340/146.3 E |
| 4,620,318 A | 10/1986 | Hill | 382/2 |
| 4,641,349 A | 2/1987 | Flom et al. | 382/2 |
| 4,876,608 A | 10/1989 | Eaton | 358/443 |
| 5,055,658 A | 10/1991 | Cockburn | 235/382 |
| 5,109,390 A | 4/1992 | Gilhousen et al. | 375/1 |
| 5,151,583 A | 9/1992 | Tokunaga et al. | 250/201.2 |
| 5,175,758 A | 12/1992 | Levanto et al. | 379/57 |
| 5,187,506 A | 2/1993 | Carter | 351/221 |
| 5,291,560 A | 3/1994 | Daugman | 382/2 |
| 5,359,669 A | 10/1994 | Shanley et al. | 382/6 |
| 5,392,297 A | 2/1995 | Bell et al. | 371/22.6 |
| 5,404,163 A | 4/1995 | Kubo | 348/142 |
| 5,448,622 A | 9/1995 | Huttunen | 379/58 |
| 5,485,486 A | 1/1996 | Gilhousen et al. | 375/205 |
| 5,572,596 A | 11/1996 | Wildes et al. | 382/117 |
| 5,581,630 A | 12/1996 | Bonneau, Jr. | 382/116 |
| 5,629,981 A | 5/1997 | Nerlikar | 380/25 |
| 5,646,709 A | 7/1997 | Carter | 351/218 |
| 5,719,950 A | 2/1998 | Osten et al. | 382/115 |
| 5,751,260 A | 5/1998 | Nappi et al. | 345/8 |
| 5,751,836 A | 5/1998 | Wildes et al. | 382/117 |
| 5,790,957 A | 8/1998 | Heidari | 455/553 |
| 6,289,113 B1 * | 11/2001 | McHugh et al. | 382/117 |

FOREIGN PATENT DOCUMENTS

| | | |
|---|---|---|
| EP | 97302580.2 | 4/1997 |
| GB | 9611787.4 | 6/1996 |
| GB | 9621900.1 | 10/1996 |
| WO | WO 97/21188 | 6/1997 |
| WO | WO 97/46978 | 12/1997 |
| WO | WO 97/46979 | 12/1997 |
| WO | WO 97/46980 | 12/1997 |
| WO | WO 98/08439 | 3/1998 |
| WO | WO 98/32093 | 7/1998 |

* cited by examiner

*Primary Examiner*—Bhavesh Mehta
(74) *Attorney, Agent, or Firm*—Woodcock Washburn LLP

(57) ABSTRACT

A compact, handheld imaging apparatus which can be used to capture high-quality iris images for identification of a person. The handheld iris imager is non-invasive and non-contacting and comprises a camera, a cold mirror, a lens, and an illuminator. The imager has sensors and indicators which assist a user in aligning and focusing the device. The imager also automatically captures the image when proper positioning is achieved. A template of the image is then transmitted to a receiver in a vehicle or other asset and compared to a database of previously stored templates of images to identify the person. The imager is part of a security module to protect access to an asset such as a vehicle or residence. The vehicle or residence cannot be unlocked and used unless a user has been identified and authorized by the imager and a controller system.

12 Claims, 9 Drawing Sheets

PORTABLE AUTHENTICATION DEVICE AND METHOD USING IRIS PATTERNS

RELATED APPLICATION DATA

This is a continuation-in-part of U.S. patent application Ser. No. 09/310,302 which was filed May 12, 1999, which is a continuation-in-part of U.S. patent application Ser. No. 09/199,369 which was filed Nov. 25, 1998.

FIELD OF THE INVENTION

The present invention relates in general to identification of physical characteristics of a human being or other animal. More particularly, the present invention relates to iris recognition.

BACKGROUND OF THE INVENTION

Various technologies are used for uniquely identifying a person in accordance with an examination of particular attributes of either the person's interior or exterior eye. One of these technologies involves the visual examination of the particular attributes of the exterior of the iris of at least one of the person's eyes. The iris of the human eye has random patterns of striations, ciliary processes, crypts, rings, furrows and other features which had been shown capable of generating highly unique biometric templates for personal identification. In this regard, reference is made to U.S. Pat. No. 4,641,349, "Iris Recognition System", issued to Flom et al., and U.S. Pat. No. 5,291,560, "Biometric Personal Identification System Based on Iris Analysis", issued to Daugman. As made clear by these patents, the visible texture of a person's iris can be used to distinguish one person from another with great accuracy. Thus, iris recognition can be used for such purposes as controlling access to a secure facility or a bank automatic teller machine, for example. An iris recognition system involves the use of an imager to video image the iris of each person attempting access, and image processing means for comparing this iris video image with a reference iris image on file in a database.

Iris identification systems have been developed that are capable of collecting images of the iris and processing them to produce biometric templates. These templates may be used to identify individual irises with extremely low error rates, on the order of 1 in $10^6$. The systems capture the iris images using stationary optical platforms that are often large, complex, and expensive. As a result their usefulness in many applications is limited. One such application is access to a vehicle or other asset such as a residence. Typically, a key is used to provide access to a vehicle or other asset. A remote doorlock control is one alternative to a key for controlling access to the vehicle. However, the remote doorlock control is limited by several factors. One factor is that possession of the remote device will provide access to the vehicle regardless of who has the device, so if the remote device is lost or stolen, the vehicle can easily be stolen as well. Another factor is that only a particular remote device(s) will start any given vehicle. If the device is lost or not with the vehicle user, the user cannot get access to the vehicle, even if he is the rightful user. An iris identification system would provide convenient access to a vehicle for authorized users, while preventing unauthorized users from accessing the vehicle. However, conventional iris identification systems are too large, complex, and expensive to be useful.

Although the art of human recognition systems is well developed, there remain some problems inherent in this technology, particularly the lack of a portable or handheld device specifically designed to solve the problems inherent in capturing a close-up, high-quality, properly focused image of the iris of the eye for use in granting access to an asset such as a vehicle or residence. Therefore, a need exists for a recognition system that overcomes the drawbacks of the prior art.

SUMMARY OF THE INVENTION

The present invention is directed to systems and methods for providing access to a vehicle or other asset. An exemplary system comprises and imager and a comparison controller system. The imager comprises iris acquisition means having a front surface for obtaining an image of an iris of an eye; a lens having an image plane disposed in front of the front surface of the iris acquisition means; a mirror disposed on a side of the lens opposite the iris acquisition means; an illuminator disposed along a side of the mirror; a first memory for storing an iris image obtained by the iris acquisition means; a processor for extracting a template from the stored iris image; and a communications interface for transmitting the template to the controller system. The controller system comprises a communications interface for receiving the template from the imager; a second memory for storing at least one template of at least one image of an iris of at least one person's eye; a processor for comparing the received template with the at least one template in the second memory to identify the person; and a lock interface coupled to the processor for receiving a command from the processor responsive to the results of the comparison. The processor sends an unlock command via the lock interface to unlock the vehicle or other asset if the comparison indicates a substantial match between the received template and the at least one template stored in the second memory.

A further embodiment within the scope of the present invention is directed to a method of providing access to a vehicle or other asset responsive to the identification of a person, comprising: (a) storing image information of the iris of at least one person's eye in a memory in a controller system; (b) illuminating an eye of an unidentified person having an iris with an imager; (c) obtaining an image of the iris of the unidentified person; (d) determining if the image is an image of sufficient quality for a step (f) of extracting; (e) repeating steps (b) through (d) until the image of sufficient quality is obtained; (f) extracting an iris template if the image is of sufficient quality; (g) transmitting the iris template from the imager to the controller system; (h) at the controller system, receiving the iris template from the imager and comparing the iris template with the stored image information to identify the unidentified person; and (i) providing access to the vehicle or other asset responsive to the result of the step of comparing.

According to aspects of the invention, access to the vehicle or other asset comprises unlocking the vehicle or other asset if the iris template substantially matches the stored image information, wherein the vehicle or other asset remains locked if the iris template does not substantially match the stored image information.

BRIEF DESCRIPTION OF THE DRAWINGS

The foregoing and other aspects of the present invention will become apparent from the following detailed description of the invention when considered in conjunction with the accompanying drawings. For the purpose of illustrating the invention, there is shown in the drawings an embodiment that is presently preferred, it being understood, however, that the invention is not limited to the specific methods and instrumentalities disclosed. In the drawings.

DESCRIPTION OF EXEMPLARY EMBODIMENTS AND BEST MODE

The present invention is directed to a compact, handheld imaging apparatus and method which can be used to capture high-quality iris images. Preferably, the imager has sensors and indicators which assist the human operator in aligning and focusing the device. The imager also automatically captures the image when proper positioning is achieved. Because it is small and compact, it is practical for integration into a system to provide access to a cellular telephone, vehicle, or other asset where it is used to authenticate user and eliminate fraud or theft. Throughout the following detailed description similar reference numbers refer to similar elements in the figures of the drawings.

Figure 1:
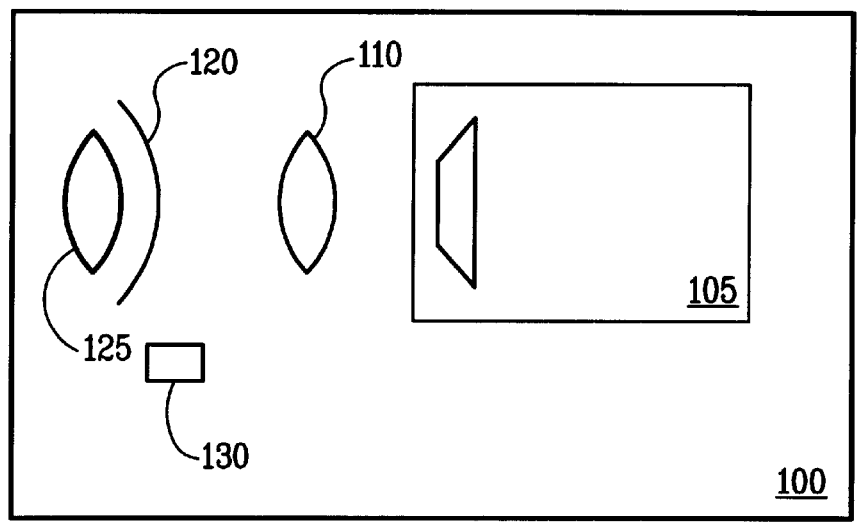
FIG. 1 is a schematic diagram of an exemplary iris imager in accordance with the present invention.

FIG. 1 illustrates a preferred embodiment of the handheld imager 100 in accordance with the present invention. The exemplary handheld, non-invasive, non-contacting iris imager comprises iris acquisition means 105, an imaging lens 110, a mirror 120, an optional diopter correction lens 125, and an illuminator 130. The imager 100 is preferably powered by a standard DC supply such as a battery or other suitable source.

The iris acquisition means 105 is preferably a conventional solid state video camera, such as a charged coupled device (CCD) or complementary metal oxide semiconductor (CMOS) device. A preferred camera is a 1/3 inch format, monochrome CCD board camera, such as Computar Model EM200. Preferably, the video camera 105 is sensitive to light of wavelengths in the range of about 400 nanometers to about 1100 nanometers, and is positioned so that its front surface coincides with the image plane of the lens 110 in front of it. In the preferred embodiment, the object plane of the lens is approximately 89 mm in front of the lens 110. More preferably, the lens 110 is an optical lens with approximately 14.2 mm focal length.

The mirror 120, preferably a concave cold mirror having a radius of curvature preferably about 276 mm, is disposed on the side of the lens 110 opposite the video camera 105 and creates a magnified virtual image of the iris behind the mirror 120. In the preferred embodiment, the mirror 120 reflects visible light with wavelengths in the range of about 400 to about 700 nanometers, and passes light having longer wavelengths, such as those in the range of about 700 to about 900 nanometers.

The illuminator 130 is positioned just outside the edge of the cold mirror 120 and is used to illuminate the iris of the subject being identified. The preferred illuminator 130 emits light having wavelengths of about 680 to about 900 nanometers. Preferably, the illuminator 130 is a miniature quartz halogen or krypton gas bulb operating at approximately 1 watt.

The imager acquires images of an iris with sufficient clarity, focus, and size for use with conventional image processing and comparison routines, preferably in less than about 3 seconds. A preferred image processing and comparison routine is described in U. S. Pat. No. 5,291,560, "Biometric Personal Identification System Based on Iris Analysis", issued to Daugman, and commonly assigned with the present invention to IriScan Inc., and incorporated herein by reference. However, any processing and comparison technique can be used with the image that is acquired at the imager, such as the image pixel correlation technique described in U.S. Pat. No. 5,572,596, "Automated, Non-Invasive Iris Recognition System and Method", issued to Wildes et al. and the techniques described in U.S. Pat. No. 4,641,349, "Iris Recognition System", issued to Flom et al., both of which are incorporated herein by reference.

Figure 2A:
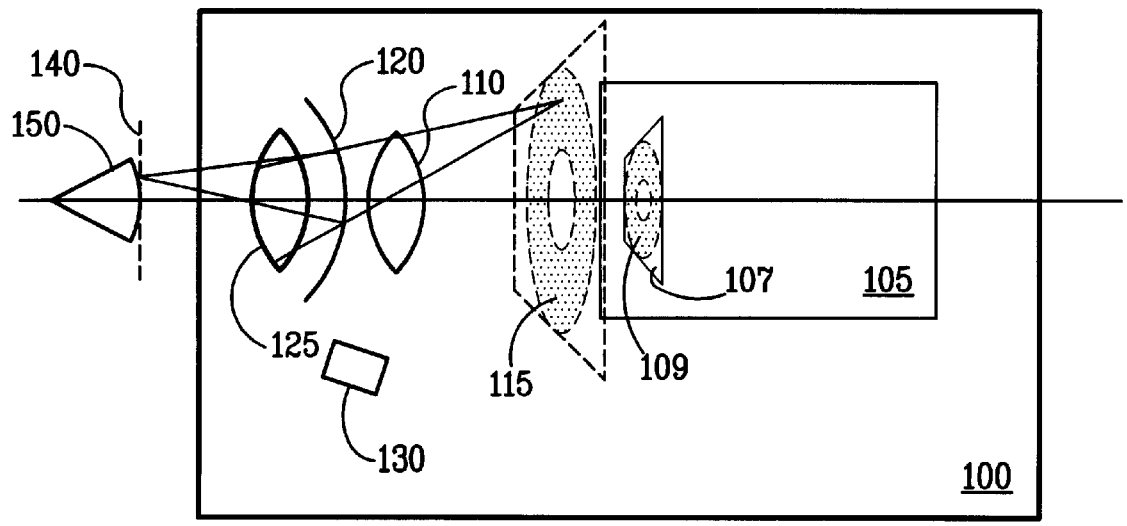
FIG. 2A is a schematic diagram of the imager of FIG. 1 shown in greater detail.

FIG. 2A shows the apparatus of FIG. 1 in greater detail. The lens 110 gives a high resolution image of the eye 150 of the user, who is positioned in front of the lens 110, so that extreme proximity between the eye 150 and the imager 100 is not required (i.e., no contact is needed between the subject and the imager 100).

The handheld iris imager comprises a solid-state image capture device and an optical system which forms an image 109 of the iris on the image capture device at the image plane of the video camera 105 and at the same time produces a virtual image 115 of the iris which the user can use to position and focus the iris image. As a result, the user can, using the same eye being imaged, see a reflected image of the iris which can be used to position the handheld imager 100 so that a good iris image (i.e., an image that can be processed and compared to those stored in a database) can be obtained.

FIG. 2A also shows an optional dioptric correction lens 125 positioned between the eye 150 and the cold mirror 120. The dioptric correction lens 125 is an adjustable optical element which corrects for the close-range focusing ability of the individual eye, which varies from subject to subject.

When the lens 125 is properly adjusted, the magnified, reflected virtual image 115 of the subject's eye appears in sharp focus to the subject at the same eye-to-mirror distance at which the subject's eye is sharply focused on the front surface of the camera. This simplifies use of the imager, because the subject simply positions the image so that the virtual image 115 of the iris appears sharply focused.

A preferred embodiment of the dioptric correction mechanism has no correction lens 125 and instead has a mechanical means (not shown) for adjusting the position of the cold mirror 120 relative to the camera lens 110. This allows the user to vary the object distance of the cold mirror 120, thus changing the eye-to-lens distance at which the virtual image 115 of the iris is sharply focused. An alternative mechanical means (not shown) allows the position of the lens 110 to be adjusted so that the camera object plane coincides with the mirror object plane.

The ability to set the dioptric correction mechanism to accommodate a particular user has a great utility if the imager is used by only one person most of the time. Once the correction is set, the user can easily position the device to obtain a sharply focused reflected image. This automatically produces a sharply focused image from the camera and substantially immediate acceptance of the image by the focus assessment processor described below. Image capture time is thereby reduced and overall convenience and utility is enhanced.

An eye 150 is positioned in front of the imager 100 (e.g., about 3.5 inches in front), as shown in FIG. 2A, and the illuminator 130 is turned on. This, in turn, illuminates the eye 150 and the iris therein. Preferably, the light having wavelengths of about 400 to about 700 nanometers is reflected by the cold mirror 120, thereby forming a magnified virtual image 115 behind the mirror 120 which the user can see through the eye being imaged. The radius of curvature of the mirror is selected so that the magnified image 115 of the eye substantially fills the user's entire field of view. Hence, when the imager 100 is positioned so that the entire eye 150 is visible, it is virtually assured that the eye 150 will be substantially centered in the object plane 140 of the camera 105. Under these conditions, the light having wavelengths of about 700 to about 900 nanometers is passed by the mirror 120 and forms an approximately centered image 109 of the eye 150 at the image plane 107 of the camera 105. The image is then captured and processed, as described below.

Although a cold mirror (one which reflects shorter wavelengths and passes longer wavelengths) is described herein, it is understood that a hot mirror (one which reflects longer wavelengths and passes shorter wavelengths) could also be used in accordance with the present invention. Such a configuration is shown in an imager 101 in FIG. 2B. The eye 150 is illuminated by an illuminator 131 emitting light having wavelengths in the range of about 680 to 900 nanometers. This light is reflected by the eye 150 and the light having wavelengths in the range of about 700 to 900 nanometers is reflected by the hot mirror 121 to be focused by the lens 111 onto the front surface of the camera 106. Light reflected from the eye 150 having shorter (visible) wavelengths in the range of about 400 to 700 nanometers passes through the hot mirror 121 and strikes a concave broadband mirror 122 which reflects light having wavelength from about 400 to 900 nanometers. This light forms a virtual image 115 of the eye 150 behind the concave mirror 122 that the user can see and use to align and focus the device, as described below.

Figure 2B:
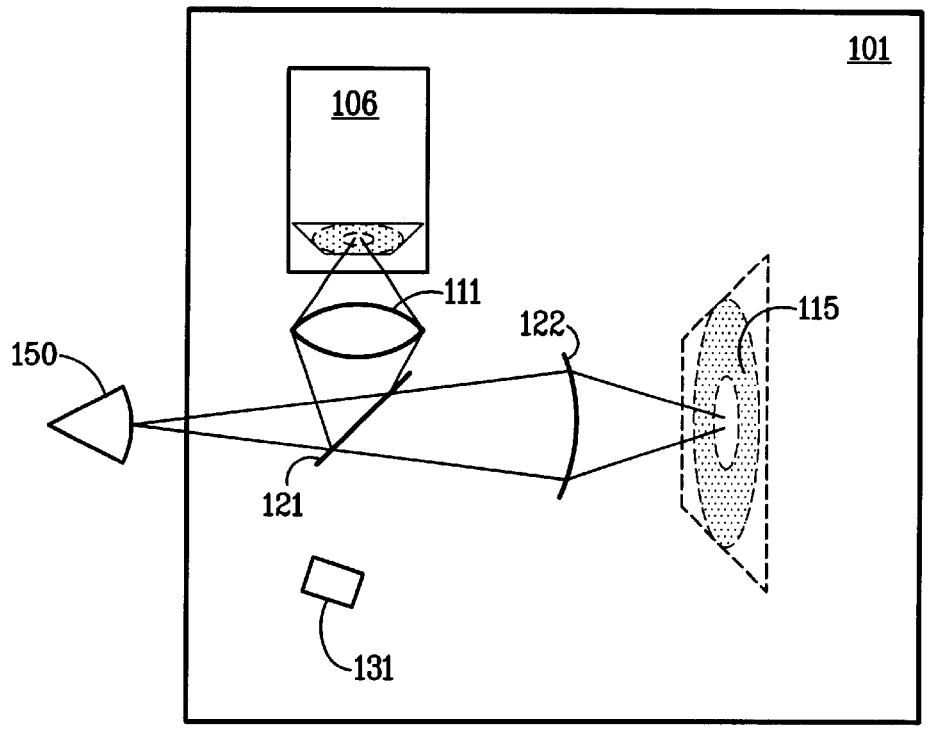
FIG. 2B is a schematic diagram of another exemplary imager in accordance with the present invention.
Figure 3:
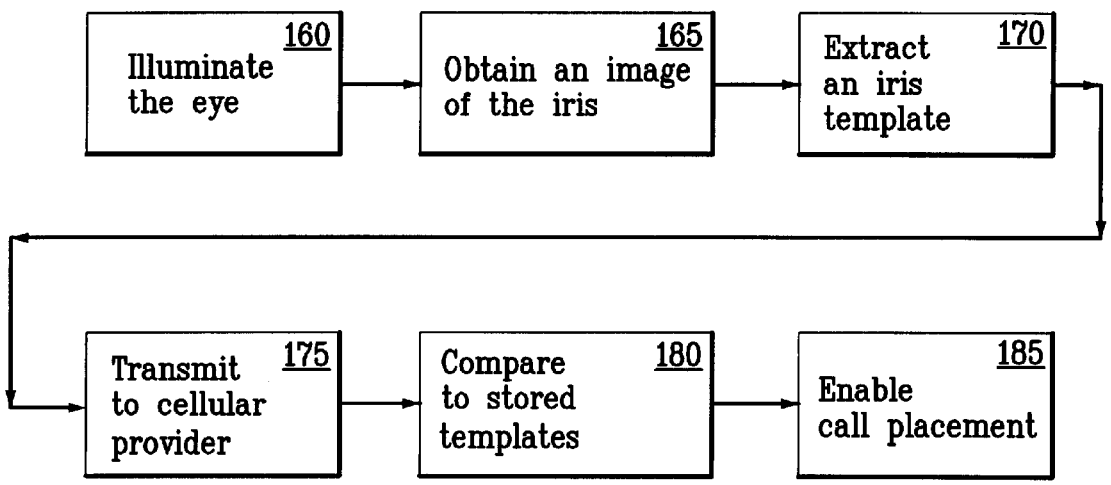
FIG. 3 is a simplified flowchart of a method of operation in accordance with the present invention.

The imager 100 of FIGS. 1 and 2A, as well as the imager of FIG. 2B, is used in a system to identify the iris image that has been captured. As shown in FIG. 3, the eye is illuminated at step 160, and an acceptable or suitable image of the iris is obtained at step 165. The image is processed to extract an iris template or code at step 170, the template or code is encrypted (optional) and, depending on the implementation, transmitted to the cellular provider (such as a central station; e.g., a Mobile Telephone Switching Office) or other comparison controller system (such as one disposed in a vehicle or residence) at step 175, and the template or code is decrypted (if necessary) and compared to pre-existing templates or codes of authorized subscribers stored in a memory or database for identification and authorization of the user at step 180. If the user is authorized, the cellular provider enables the call placement at step 185 or the user is provided access to the vehicle or other asset. In the case of a cellular telephone, the cellular provider can either enable the call at the central station or send a signal to the telephone processor directing it to unlock the telephone.

Figure 4:
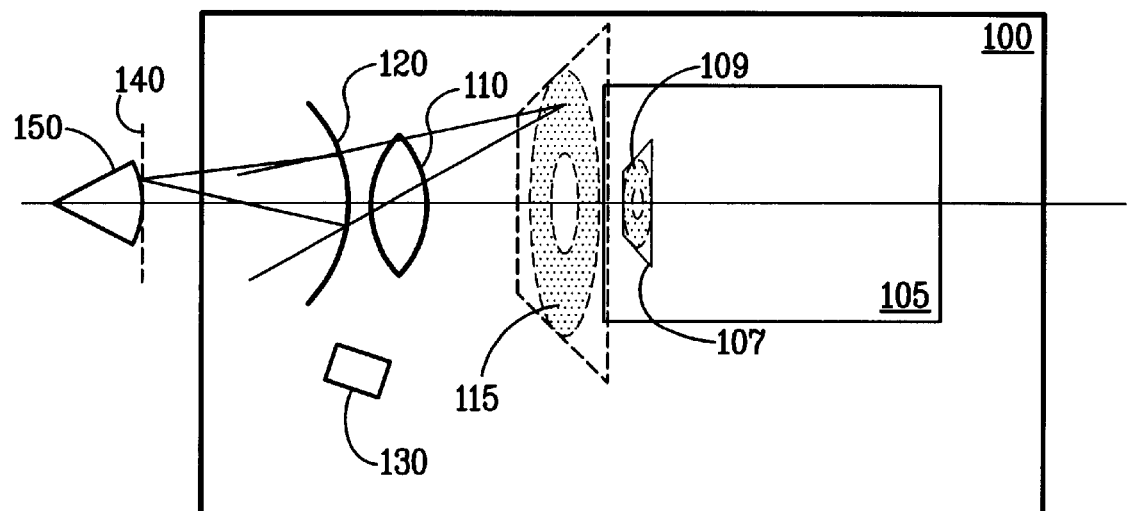
FIG. 4 is a schematic diagram of an exemplary iris image recognition system in accordance with the present invention.

FIG. 4 is a schematic diagram of an exemplary iris image recognition system in accordance with the present invention. The imager 100 is coupled to a microprocessor 210 that performs the processing and encryption. The microprocessor 210 resides in a cellular telephone 200.

The microprocessor 210 is coupled to the imager 100 via conventional cables and/or printed circuit boards (PCBs) that are incorporated into the telephone 200. Other conventional means for coupling the imager 100 and the microprocessor 210 can be employed. The microprocessor 210 controls the imager 100 and runs software held in read only memory (ROM) 205. The processor 210 is connected via a bus 207 to the ROM 205, a random access memory (RAM) 232, another memory such as an erasable programmable ROM (EPROM) 230, and an input/output (I/O) controller 225. The RAM 232 is large enough to hold at least one captured image of an iris. The I/O controller 225 is connected to the appropriate circuitry and drivers (not shown) for issuing commands to control the imager 100.

The imager 100 preferably uses a digital camera and transmits digital images directly to the processing unit 210. "On/off" data is transmitted from the imager 100 to the processor 210 to initiate the image acquisition function. A digital image could be provided if a digital camera is used.

The image processing consists of a number of image processing steps (such as those described in U.S. Pat. Nos. 5,291,560 and 5,572,596, which are herein incorporated by reference) which lead to extraction of a unique and highly specific digital biometric template that can be used to identify the individual based on intensity patterns within the iris. The biometric template is transmitted to the cellular provider where it is compared against other templates stored in a memory or database. The database stores selected data representing images of the iris of a plurality of subjects. A match of the biometric template with a template stored in the database identifies the subject whose iris is being imaged.

Although an image of the eye is reflected back to the subject in mirror 120, this may not provide the desired feedback to the user to enable the user to properly position the imager so that a suitable iris image is obtained. For example, a user may be a novice in using and positioning the imager 100 with respect to the eye 150, or the user may be attempting to image the eye of another subject with the imager. Thus, preferably, the imager 100 comprises a passive feedback mechanism to guide the user in positioning the eye 150 to an optimum location to allow acquisition of a suitable image.

Figure 5:
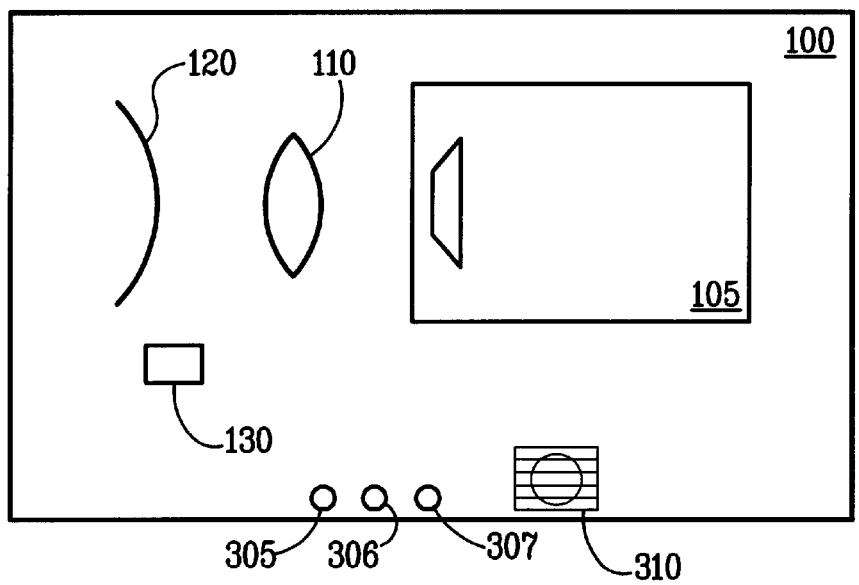
FIG. 5 is a schematic diagram of an exemplary iris imager having visual and aural indicators in accordance with the present invention.

The passive feedback mechanism is an indicator or combination of indicators that provides, on a near real-time basis, an indication to the user that an adequate iris image has or has not been obtained. FIG. 5 is a schematic diagram of an exemplary iris image recognition system that includes position indicators in accordance with the present invention. Preferably, the indicator is visible and/or audible, such as, for example, an indicator lamp 305 (e.g., a light emitting diode (LED)) that lights when an acceptable image has been captured (i.e., "image acquired"), and a aural indicator via a speaker 310, such as a beep or other tone, that sounds periodically until an acceptable image has been captured (i.e., "imaging in progress").

Additional indicators 306, 307 can be also be used, either alone or in combination, for such indications as "subject identified-accept" and "subject not identified -reject". These indications would be activated pursuant to the results of the processing and comparison performed at the database server at the cellular provider, as described above with respect to FIG. 3. Alternatively, other display devices, such as liquid crystal displays used for other purposes within the telephone, could be used as indicators.

The imager 100 also preferably has an on/off switch (not shown), such as a pushbutton, for powering up the imager and initiating the image acquisition process. Power for the imager 100 is preferably supplied by a battery. The imager 100 receives and acts on instructions from the processor 210 o perform functions such as lighting or turning off the indicator lamp(s) 305, providing the audible signals via the speaker 310, and lighting the 'accept' and 'reject' indicators.

Figure 6:
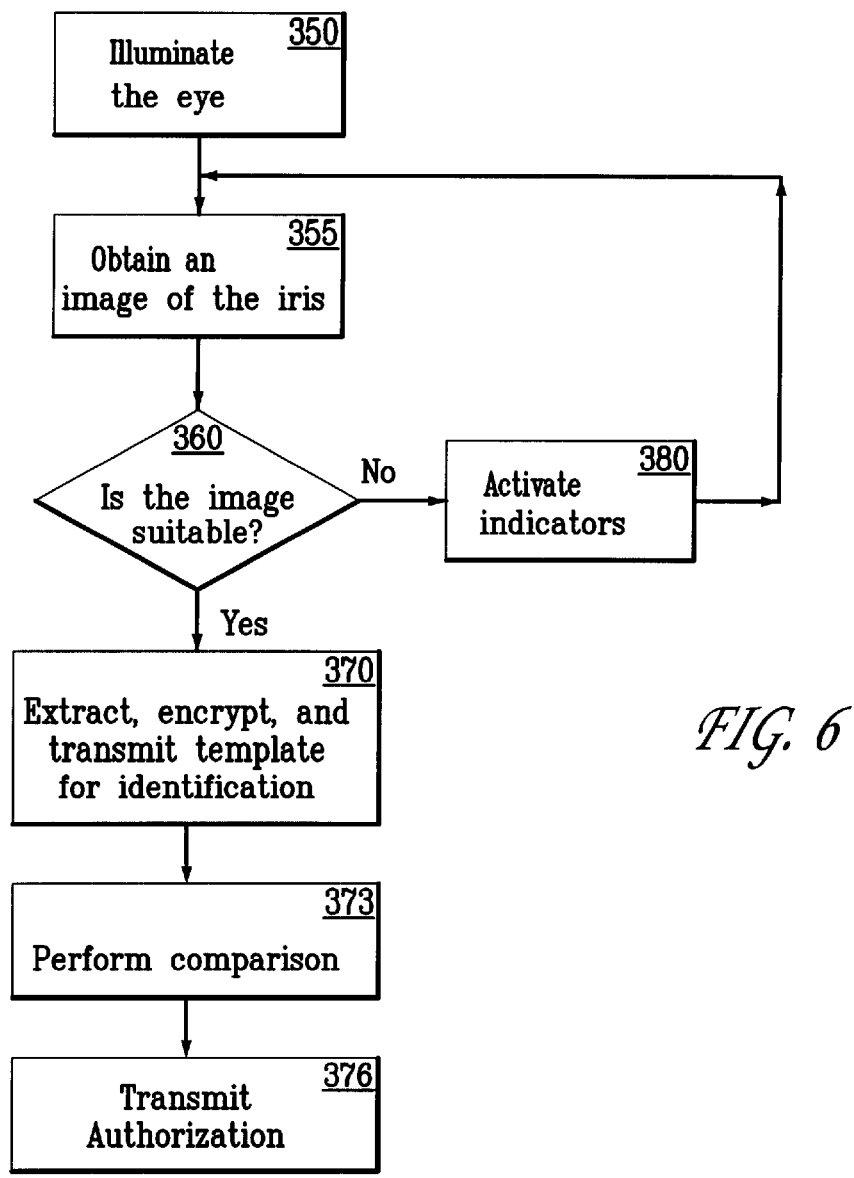
FIG. 6 is a more detailed flow chart of a method of operation in accordance with the present invention.

FIG. 6 is a more detailed flow chart of a method of operation in accordance with the present invention. The eye is illuminated at step 350 and an image of the iris is obtained at step 355. At step 360, it is determined if the image is suitable for use with the image processing and comparison routines. If the image is suitable, the image is passed to the processor for further processing, at step 370, and transmission to the cellular provider or other comparison controller system residing, for example, in a vehicle, residence, or office. A comparison of the template to the templates stored in a database at the cellular provider other comparison controller system is performed at step 373. If the comparison provides a positive match, then authorization is granted at step 376 for the user to use the phone or gain access to the vehicle or other asset. If the comparison does not provide a positive match, then authorization is not granted for the user to use the phone or gain access to the vehicle or other asset.

If the image is not suitable at step 360, then at step 380, the indicator(s) is activated (e.g., a beep sound is issued), and processing continues at step 355 (i.e., another image is obtained).

Figure 7:
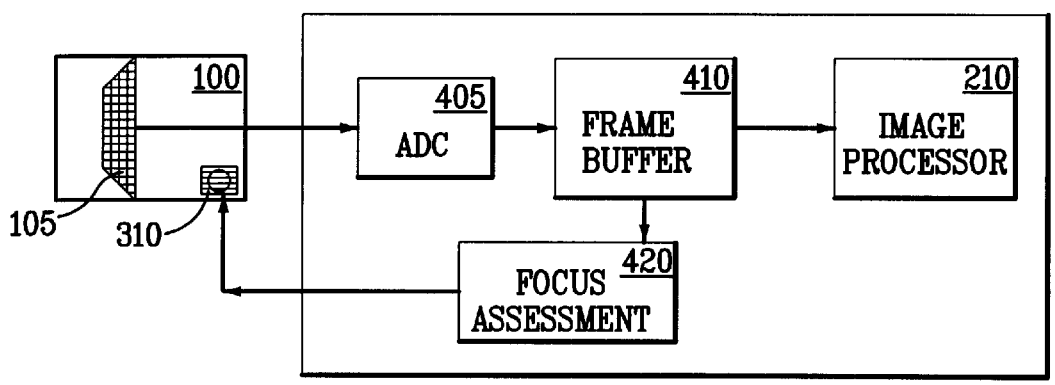
FIG. 7 is a schematic diagram of an exemplary iris image recognition system having a focus assessment processor in accordance with the present invention.

Because the eye's own focusing system automatically adjusts to bring the virtual image 115 into sharp focus to the user, it cannot be relied upon to always accurately focus the eye image on the camera 105. For this purpose, a focus assessment system is used in one embodiment, as shown in FIG. 7. Digital video image information from the imaging device 100 is stored in a frame buffer memory 410, such as a RAM similar to RAM 232 described above with respect to FIG. 4, and capable of storing one complete frame of digitized video information. A focus assessment processor 420 accesses the digitized image information and applies certain measurement algorithms which are disclosed in a co-pending application entitled "Video-Rate Focus Assessment", Ser. No. 60/109,960 and incorporated herein by reference. The output of the focus assessment is used to control an indicator, such as the audible indicator 310. As long as the focus assessment processor 420 determines that the captured image is not acceptable for further processing and comparison, the audible indicator 310 is directed to emit periodic sounds to alert the user. Images are repeatedly acquired and assessed until an acceptable one is received. After an acceptable iris image has been received, the audible indicator 310 is turned off and the final image is retained for further processing and comparison, for example, by the microprocessor 210, as described above.

Any known technique for image focusing can be used with the imager of the present invention, such as those described in U.S. Pat. No. 4,876,608, entitled "Focus and Signal to Noise Measurement Routines in Input Scanners", issued to Eaton, U.S. Pat. No. 5,151,583, entitled "Focus Adjustment Device Having Restricting Means for Restricting a Selecting Action According to the Degree of Nearness of a Distance Measurement", issued to Tokunaga et al., and U.S. Pat. No. 5,404,163, entitled "In-Focus Detection Method and Method and Apparatus Using the Same for Non Contact Displacement Measurement", issued to Kubo. The preferred system and method for focus assessment is described below.

A focus score is computed for each video frame (i.e., each captured image). If the focus score exceeds a predetermined value, then it is determined that the image is focused enough for further processing and comparison. If the focus score does not exceed the predetermined value, then it is determined that the image is not focused enough for further processing, and an indicator (such as indicator 310, described with respect to FIG. 5) is activated and a further image is captured. Alternatively, a sequence of image frames can be obtained that cycle through a range of focus distances strobed at the video frame-rate, and the focus score computed for each frame can enable the selection of the best focused frame within the sequence of frames. For example, by obtaining image frames at each of several different lens settings and then fitting a spline curve to their respective focus scores one can predict the lens position that would deliver substantially the sharpest focus, by setting the derivative of the parameterized spline curve to zero and then solving the equation for position.

Specific implementation features of the preferred focus assessment system and method which enable its real-time operation, include (1) the computation of quantities in the 2D Fourier domain, without needing to compute an actual 2D Fourier Transform of an image (this avoids the need for approximately 2.25 million floating-point operations required for an FFT (Fast Fourier Transform) on a 500×500 pixel image, as the computational complexity of an FFT on n ×n data is $O(n^2\log_2 n)$); (2) only 6,400 integer multiplications (squarings) are performed, which in turn can be eliminated altogether by using small look-up tables; (3) no floating-point operations are required; (4) computation of focus scores is based upon simple algebraic combinations of pixel values within local closed neighborhoods, repeated across regions of the image; and (5) these operations not only allow the algorithm to execute in real-time, but it also enables a straightforward implementation in simple, low-cost, hardware devices that could be embedded within a digital camera or frame grabber.

Preferably, the focus assessment processor 420 is fast enough to determine a focus score for each frame in a video image stream in less than the time it takes to acquire a new frame (e.g., approximately 25 ms). The frame-by-frame focus scores can be used to control a moving lens element for rapid and accurate focus control, or alternatively, to select which of several frames in a video stream is the one in best focus. The rapid selection of well-focused video frames for further processing, such as image analysis and pattern recognition, is important in real-time computer vision because it prevents wasting processing time on poorly-focused images.

The preferred focus assessment processor measures the focus quality of video images at standard rates of 25 (PAL) or 30 (NTSC) frames per second.

It is contemplated that the focus assessment processor 420 can be implemented in a general purpose personal computer (PC) or by a dedicated, low cost processor which is small enough to be incorporated into the camera electronics.

The processing of a video frame results in the return of an integer value (on a scale between 0 and 100) reflecting the quality of focus; the larger the value of the integer, the better the focus. A value of 0 indicates a completely defocused image whereas the value of 100 indicates maximum focus quality. A predetermined threshold is used to determine whether an image is sufficiently focused or whether another image needs to be retrieved. For example, values greater than about 40 can indicate sufficient quality of focus to warrant further image processing, while values less than about 40 cause a new image frame to be grabbed, and optional feedback provided to the focusing mechanism, if one exists, or to the subject controlling the camera position (via the indicator 310, for example).

Optical defocus is a phenomenon of the 2D Fourier domain. An image represented as a 2D function of the real plane, I(x,y), has a 2D Fourier Transform F($\mu$, v) defined as shown in equation 1.

$$F(\mu, v) = \frac{1}{(2\pi)^2} \int_x \int_y I(x, y) e^{i(\mu x + v y)} dx dy \quad (1)$$

In the image domain, defocus is preferably represented as convolution by the 2D point-spread function of the defocused optics. This in turn may be modeled as a Gaussian whose space constant is proportional to the degree of defocus. Thus, for perfectly focused optics, the optical point-spread function shrinks almost to a delta function, and convolution with a delta function causes no change to the image. Progressively defocused optics equates to convolving with a wider and wider point-spread function, which averages together whole neighborhoods of pixels by such a weighting function, thereby producing an increasingly blurred image.

If the convolving optical point-spread function causing defocus is modeled as a Gaussian whose width represents the degree of defocus, then defocus is equivalent to multiplying the 2D Fourier Transform of a perfectly focused image with the 2D Fourier Transform of the "defocusing" (convolving) Gaussian. This latter quantity is itself just another 2D Gaussian but in the Fourier domain, and its space constant ($\sigma$) there is the reciprocal of that of the image-domain convolving Gaussian that represented the optical point-spread function. The preferred focus assessment processor uses (1) the duality of convolution and multiplication in the two domains; (2) the fact that a Gaussian has a Fourier Transform which is itself a Gaussian, but with the reciprocal width because of (3) the Similarity Theorem. Thus, the 2D Fourier Transform $D_\sigma(\mu,v)$ of an image defocused to degree $\sigma$ is related to F($\mu$,v), the 2D Fourier Transform of the corresponding in-focus image, as given by equation 2.

$$D_\sigma(\mu, v) = e^{-\left(\frac{\mu^2 + v^2}{\sigma^2}\right)} F(\mu, v) \quad (2)$$

From the above equation, the effect of defocus is to attenuate primarily the highest frequencies in the image, and that lower frequency components are virtually unaffected by defocus since the exponential term approaches unity as the frequencies ($\mu$,v) become small. For simplicity, the present description has assumed isotropic optics and isotropic blur, and the optical point-spread function has been described as a Gaussian. However, the analysis can readily be generalized to non-Gaussian and to anisotropic optical point-spread functions.

Thus, an effective way to estimate the quality of focus of an image is to measure its total amount of energy in the 2D Fourier domain at high spatial frequencies, since these are the most attenuated by defocus. One may also perform a kind of "contrast normalization" to make such a spectrally-based focus measure independent of image content, by comparing the ratio of energy in the highest frequency bands to that in slightly lower frequency bands. Such spectrally-based energy measurements are facilitated by exploiting Lord Rayleigh's theorem for conserved total power in the two domains, shown in equation 3.

$$\int_{-\infty}^{+\infty} \int_{-\infty}^{+\infty} |I(x, y)|^2 dx dy = \int_{-\infty}^{+\infty} \int_{-\infty}^{+\infty} |F(\mu, v)|^2 d\mu dv \quad (3)$$

Thus, high-pass filtering or band-pass filtering an image at a ring of high spatial frequency (using only convolution in the 2D image domain) and measuring the residual energy, is equivalent to making the corresponding energy measurement in the high frequency bands of the 2D Fourier domain. The appropriate measurements in the 2D Fourier domain to assess focus can be performed without computing a time-consuming 2D Fourier Transform. Indeed, the measurements can be performed without even a single floating-point operation, and even without any multiplications if appropriate convolution kernels and look-up tables are used.

A real-time procedure for focus assessment based on these theoretical principles is used in the focus assessment processor 420. It executes much faster than the video frame-rate, and so real-time focus assessments can be made on a frame-by-frame basis. These can be used either to control the position of a focusing lens element, or alternatively as a type of autofocus system in which frames are grabbed at a variety of focal depths in order to select only the best one for processing, or to prevent time being wasted on processing image frames which are assessed to be in poor focus.

The 2D spectral measurements described above can be implemented by convolving an image with the following convolution kernel, in which pixel values within a predetermined region, such as, for example, an (8×8) neighborhood, are added together with the weights indicated in each of the cells:

| -1 | -1 | -1 | -1 | -1 | -1 | -1 | -1 |
| -1 | -1 | -1 | -1 | -1 | -1 | -1 | -1 |
| -1 | -1 | +3 | +3 | +3 | +3 | -1 | -1 |
| -1 | -1 | +3 | +3 | +3 | +3 | -1 | -1 |
| -1 | -1 | +3 | +3 | +3 | +3 | -1 | -1 |
| -1 | -1 | +3 | +3 | +3 | +3 | -1 | -1 |
| -1 | -1 | -1 | -1 | -1 | -1 | -1 | -1 |
| -1 | -1 | -1 | -1 | -1 | -1 | -1 | -1 |

It should be noted that no pixel-by-pixel multiplications are needed in order to impose these weights. Rather, the pixels in the central region are added together, such as the (4×4) square, that sum is tripled, and then all pixel values in the outer two pairs of rows and columns are subtracted from the tripled sum. The result is squared and added to an accumulator, thus implementing the left-hand side of equation (3) above for this local region of the image. The complete (8×8) convolution kernel is then moved to a new position in the image, along a sampling grid that selects every 4th row and every 4th column, and the operation is repeated. Thus, to assess the quality of focus within the central (320×320) region of an image, this set of 64 pixel summations followed by a squaring operation is repeated a total of $(320/4)^2$=6,400 times.

In the 2D Fourier domain, the spectral consequences of this operation can be appreciated by examining the 2D Fourier Transform of the convolution kernel above. The kernel is equivalent to the superposition of two centered square box functions, one of size (8×8) and amplitude -1, and the other of size (4×4) and amplitude +4 (for the central region in which they overlap, the two therefore sum to +3). The 2D Fourier Transform of each of these square functions is a 2D "sinc" function, whose size parameters differ by a factor of two in each of the dimensions and whose amplitudes are equal but opposite, because the two component boxes have equal but opposite volumes. Thus, the overall kernel has a 2D Fourier Transform $K(\mu,v)$ which is the difference of two differently-sized 2D sinc functions, as given by equation 4.

$$K(\mu, v) = \frac{\sin(\mu)\sin(v)}{\pi^2 \mu v} - \frac{\sin(2\mu)\sin(2v)}{4\pi^2 \mu v} \quad (4)$$

This is a high-pass (or ultimately a band-pass) filter, selecting only a high range of spatial frequencies in all orientations. Towards its center, corresponding to very low spatial frequencies, its value approaches zero (as can also be inferred from the fact that the sum of all pixel weights in the convolution kernel shown above is zero). Thus, low frequencies play little or no role in computing a focus score, and only relatively high frequencies contribute significantly to the computation of a focus score. Equation (3) shows that summing the squares of all the local convolution sums across the image is equivalent to summing the total amount of high frequency energy in the 2D Fourier Transform of the image. The action of the convolution kernel is to impose the above power spectral weighting function so that primarily high frequency energy is measured.

Finally, the summated 2D spectral energy is passed through a compressive nonlinearity of the form $f(x)=100 \, x^2/(x^2+c^2)$ in order to generate a normalized focus score in the range of 0 to 100 for any image.

The focus assessment technique is applied immediately after each image frame is digitized and stored in the frame buffer memory 410 in order to assess whether the focus quality is sufficient to warrant any further processing. If the calculated focus quality value of the captured image is greater than or equal to a predetermined value, the image is passed to applicable programs for further processing, for example for extraction of a biometric template. The focus assessment technique can be used to compare the relative focus of an entire series of images in order to select the one most in-focus (i.e. having the highest focus assessment score), as well as to measure a single image.

The focus assessment technique can be used to provide a feedback indication to a system user who controls the position of the imager relative to the object being imaged.

This can be accomplished by activating an indicator which would continue, while successive images are captured and their focus assessed, until the focus assessment score exceeds a predetermined value. At this point, the indicator is deactivated and the last image captured is transferred to the image processor 210 where it is processed to extract the biometric template.

The application of the focus assessment technique in combination with the feedback indicator helps resolve the man-machine interface problems associated with the use of digital imaging devices on the eye. Individuals using the system are provided positive, objective indicators and feedback as to the quality of image focus. The focus assessment processor can also be used in any situation where it is required to determine the quality of focus of video images at industry standard frame rates (NTSC and PAL).

Thus, the image is obtained at the imager and transmitted to an analog to digital converter 405. The digitized video information is then stored in a frame buffer memory 410. The focus assessment processor 420 isolates the central 320×320 region of the image. 8×8 pixel blocks (each pixel is in only one block) are then processed by first summing pixels in the central 4×4 region, tripling that sum, and then subtracting from this value all the pixel values in the outer two pairs of rows and columns. This result is then squared. This process is performed on each 8×8 block, and the results are summed. After the entire image has been processed, the summed result is compressed nonlinearly to generate a focus score between 0 and 100. This score is then compared to a predetermined number for determining if the indicator 310 should be activated.

The focus assessment is preferably performed by the microprocessor 210, or it can be a separate processor element within the telephone.

It is contemplated that in addition to the focus assessment processor, an auto-focus lens system could be used in the present invention. The results of the focus assessment control the lens system, thereby automatically adjusting focus to produce an optimal image. This would place less of a premium on the accuracy with which the user positions the eye, and would be helpful if the user could not see or hear the indicators described above.

Figure 8:
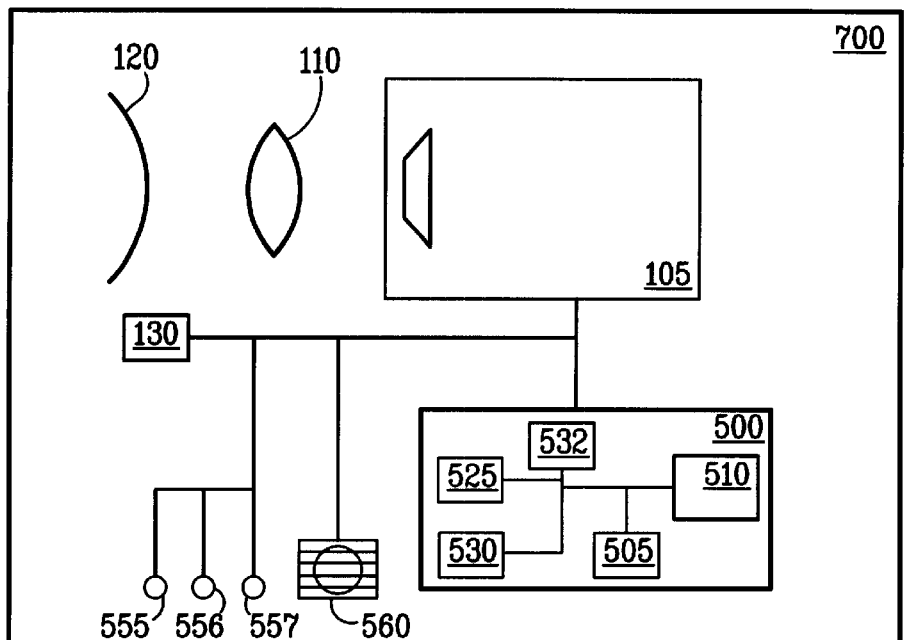
FIG. 8 is a schematic diagram of an exemplary iris imager incorporated into a telephone in accordance with the present invention.

The iris imager of the present invention can be used as a security module for electronic devices such as a telephone or for assets such as vehicles, boats, residences, and offices. FIG. 8 is a schematic diagram of an exemplary iris imager incorporated into a telephone in accordance with the present invention. The imager 700 comprises the camera 105, lens 110, mirror 120, and illuminator 130, as described above with respect to FIG. 1.

The imager 700 also comprises visible indicators 555, 556, 557, which are similar to indicators 305, 306, 307, respectively, described above with respect to FIG. 5. An audible indicator 560, similar to indicator 310, is also disposed within the imager 700. The imager 700 further comprises electronics and circuitry 500 for processing and comparing the obtained image. The electronics and circuitry 500 comprises a microprocessor 510 (similar to microprocessor 210) that controls the imager 700 along with an I/O controller 525 and runs software held in a ROM 505. The processor 510 is connected to the ROM 505, a RAM 532 that is capable of storing at least one captured image or an iris, another memory 530, such as an EPROM, for storing a plurality of biometric templates or iris images that are to be compared with the captured iris image. The electronics and circuitry 500 is also connected to the camera 105, the illuminator 130, and the indicators 555, 556, 557, 560 for controlling these elements of the imager 700. The processor can also comprise a focus assessment processor, similar to the focus assessment processor 420.

It should be noted that in the embodiment of FIG. 8, the database memory 530 of templates is stored within the imager 700 and not at a central station (as described, for example, with respect to FIG. 4), as is the processor 510 used in the comparison. In the embodiment of FIG. 8, the comparison of the captured image template with the stored templates takes place locally within the telephone, and the biometric template is not sent to the central station for comparison or authentication. Instead, preferably, a code is inserted into the call set-up protocol and transmitted to the central station server, as described below.

The imager 700 is coupled to telephone electronics 570 for transmitting encrypted or unencrypted data to another telephone or system via an antenna. The telephone electronics 570 is essentially a telephone and is preferably a conventional cell phone having telephone electronics and is connected to a transmission antenna. Preferably, a conventional voltage regulator (not shown) provides the appropriate operating voltage to the imager 700 from the power supply (e.g., a battery) of the phone.

Figure 9A:
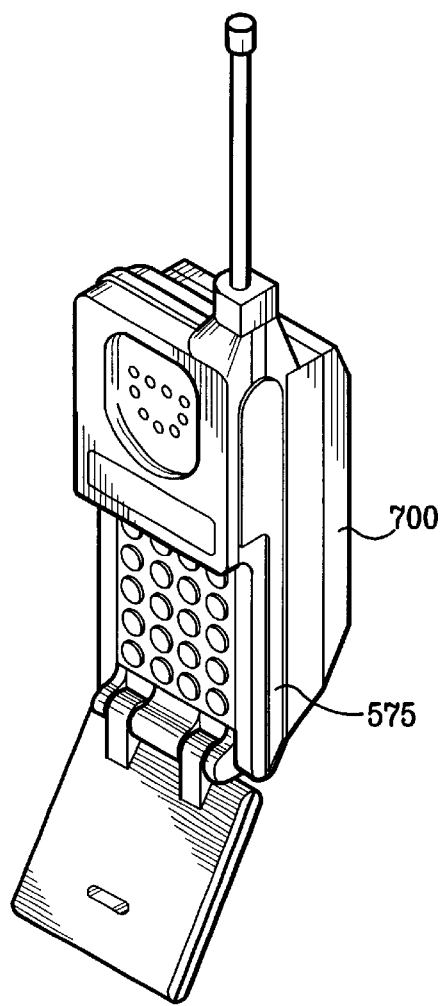
FIG. 9A is an isometric view of an exemplary telecommunications iris imager and telephone in accordance with the present invention.

The imager 700 of the present invention can be incorporated into a handset of a telephone 575, as shown in FIG. 9A. The present invention can be incorporated into a conventional digital cell phone, as shown in FIG. 9A, such as those manufactured by Qualcomm or Nokia, or a conventional wired phone. U.S. Pat. No. 5,448,622, "Cellular Telephone With Plural Telephone Numbers", issued to Huttunen, and U.S. Pat. No. 5,790,957, "Speech Recall In Cellular Telephone", issued to Heidari, describe cellular telephones and telephone electronics and circuitry, and both of which are incorporated herein by reference.

Figure 9B:
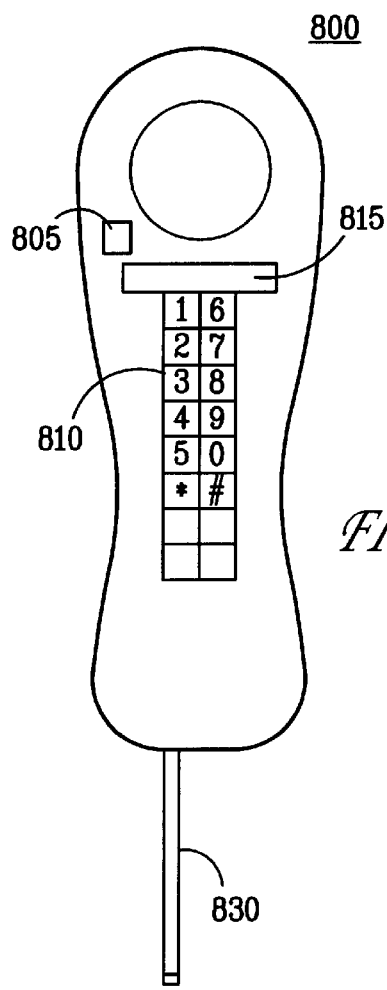
FIGS. 9B, 9C, and 9D show rear, side, and front elevational views of another exemplary device in which the imager of the present invention can be incorporated.
Figure 9C:
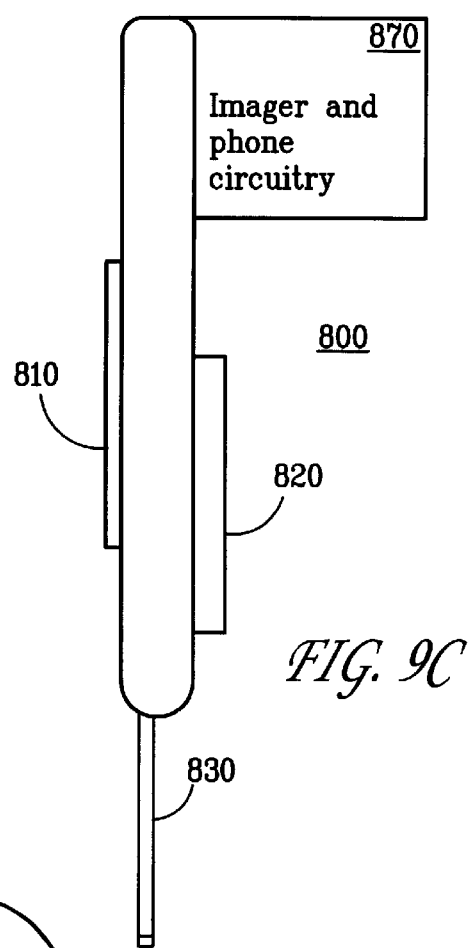
Figure 9D:
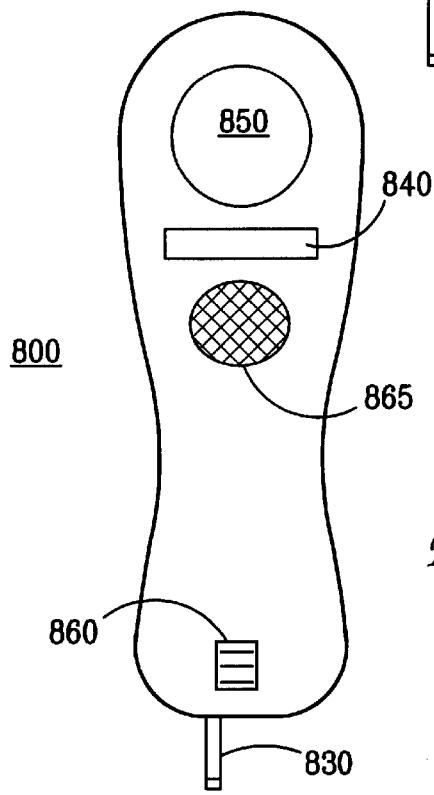

FIGS. 9B, 9C, and 9D show rear, side, and front elevational views of another exemplary device 800, also referred to as an IRISPHONE™, in which the imager of the present invention can be incorporated. A keypad 810 is used to enter phone numbers, etc., which are displayed on a display 815, such as an LCD, and a power supply 820 is preferably a re-chargeable battery. A transmission antenna 830 is also provided. An illuminator 840, similar to the illuminator 130, and a mirror 850, similar to the mirror 120 are provided on the front of the device 800. Also provided on the front of the device 800 is a microphone 860 and a speaker 865, for use in communications and as an indicator, similar to the indicator 310, described above. A switch or button 805 is used as an activator to begin iris image capture. The imager and phone circuitry 870 is encased within the device 800.

Figure 10:
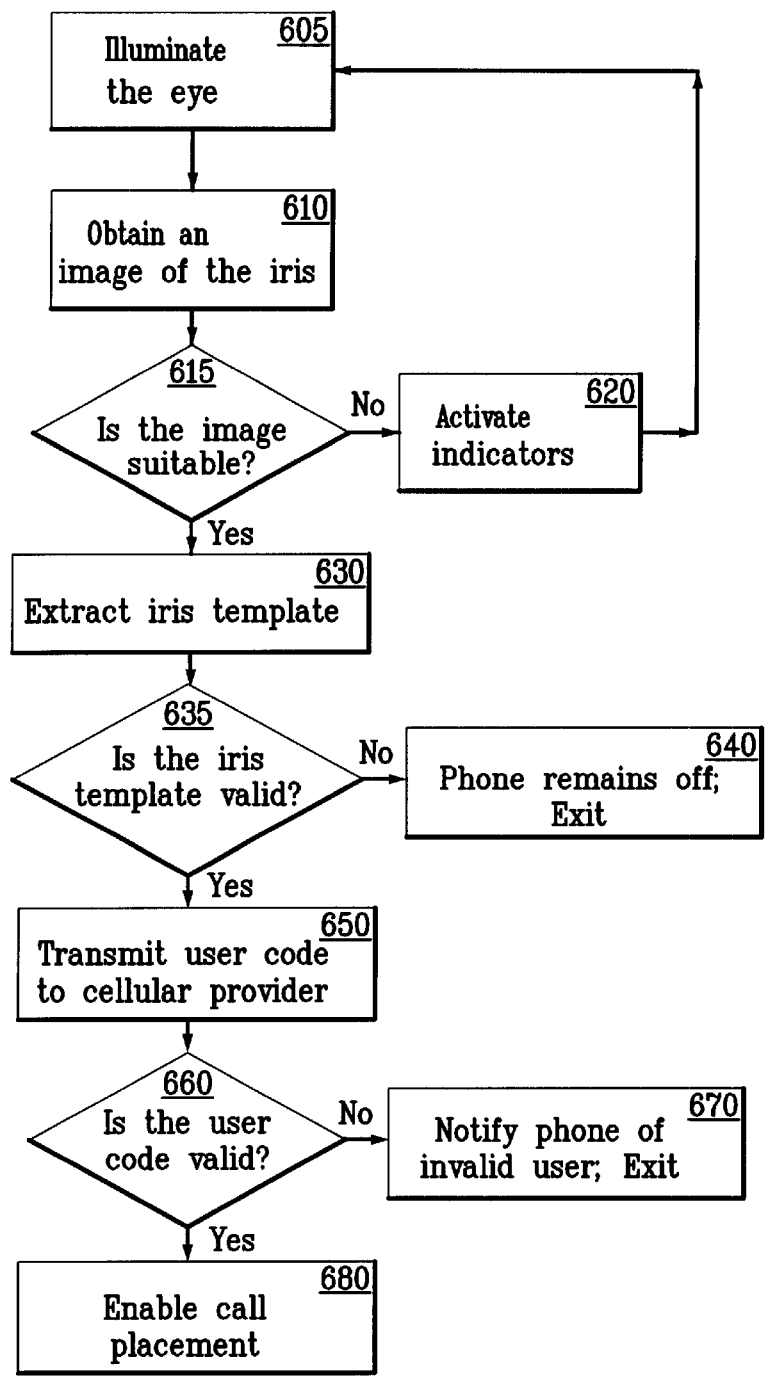
FIG. 10 is a flow diagram of an exemplary method of operation of a telecommunications iris imager in accordance with the present invention.

FIG. 10 is a flow diagram of an exemplary method of operation of a telecommunications iris imager in accordance with the present invention. A user desiring to make a telephone call first unlocks the telephone by having his iris identified by the imager residing within the phone. The eye, and thus the iris, are illuminated at step 605. An image is obtained of the iris at step 610. At step 615, it is determined if the image is suitable for further processing and comparison, as described above. If the image is not suitable, the appropriate indicators are activated at step 620, and processing returns to step 610 with the capture of another iris image.

If the captured image is suitable for further processing, the image is processed at step 630 (an indicator can be activated to alert the user that a suitable image has been captured) to extract an iris template also referred to as an IRISCODE™, comprising a 512 byte code for example. The extracted template is compared to the stored images residing in a database, for example, in a memory 530, at step 635. If the iris template is invalid (i.e., if there is no match between the captured image and the stored images), at step 640, the phone remains off (locked), and the imaging routine exits. Optionally, indicators can also be activated. In this manner, the telephone remains locked, and cannot be used because it is determined that the user is unauthorized.

Figure 11:
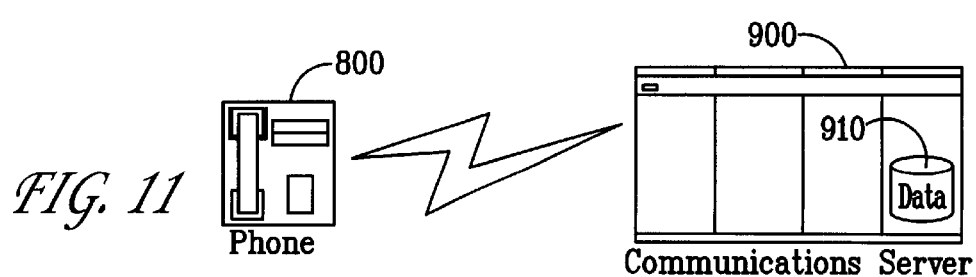
FIG. 11 is a diagram of a phone and communications server in communication with each other in accordance with the present invention.

If the iris template is valid at step 635 (i.e., there is a match between the captured image and the stored images, and thus the identity of the user has been confirmed by the imager), the phone is turned on (unlocked), an indicator can be activated, and a user code is transmitted to the service provider (e.g., the central station server 900, as shown in FIG. 11) at step 650. The user code is generated and is inserted into the call set-up protocol and transmitted to the server 900.

At step 660, the server authenticates the user code against stored or pre-enrolled codes that are stored in a database 910 at the server site. If the code is invalid, then the user is not authorized to place a call, an indicator is activated at the phone, and the routine exits at step 670. If the code is valid, then the user can use the phone to place a call at step 680. The phone can be returned to its locked, secure state either upon being powered down or upon completion of the phone call.

Thus, in accordance with the present invention, the server can bill against the user's identity (responsive to the IRISCODE™) and not the phone number. Thus, different users can use the same phone, and be separately billed, according to the identities that are stored at the server. This provides an additional level of security and user validation.

It should be noted that any call set-up protocol can be used with the present invention, including GSM, TAC, and AMPS. For example, in the Group Speciale Mobile (GSM) cellphone architecture, an "Intel Architecture" microprocessor and "Intel SmartVoltage" flash memory are preferred components. The basis of this technology is a microprocessor, such as the Intel 386 microprocessor. The preferred memory is a non-volatile, re-writeable, low voltage flash memory that enables computer-like functions. In the case of a Nokia cellphone, for example, a 4-Mbit flash memory storage device stores the GSM protocol. Intel's 16-Mbit flash devices can store such things as phone numbers, fax numbers, calendar information, as well as a Graphical User's Interface (GUI) operating system. Similarly, each IRISCODE™ (e.g., 512 bytes) of the users can be stored in these flash memory devices. Preferably, about 40 pairs of IRISCODEs (one IRISCODE™ for the left eye and one IRISCODE™ for the right eye for each user) can be stored in the 4-Mbit devices and about 160 pairs of IRISCODEs can be stored in the 16-Mbit devices.

The operating system performs such functions as: (1) retrieve the live IRISCODE™ from the IRISPHONE™ image, (2) compare the "live" IRISCODE™ against the IRISCODE™ database stored in the memory (e.g., flash memory), and (3) transfer, upon positive identification, the authentication into the GSM protocol for transport to the wireless GSM server. This is done in a manner similar to the manner in which the Electronic Serial Number (ESN) is authenticated.

The Wireless Application Protocol (WAP), along with the Wireless Application Environment (WAE), have been developed to extend Internet content and advanced services to the cellphone industry. A wireless IRISPHONE™ captures an IRISCODE™ using the WAE user agent that sends the code to the cellphone memory for local authentication. An encoded request for authentication and identity is then sent to the origin server. An encoded positive identification or negative identification is returned, and either allows the user to make calls via identity-based billing or disallows all calls. For example, the call reject function would be used to reject the identity of an individual if the live IRISCODE™ did not match any stored value. The WAP Mark-up Language (WML) allows for user defined fields such as IRISCODEs.

The Electronic Business Card Format of WAP/WAE is compatible with a 512 byte IRISCODE™. The IRISCODE™ can be stored on a card instead of in flash memory.

Some applications that can use the imager of the present invention are bank automated teller machines, computer workstations, and handicapped equipped access points. Also, a store clerk could verify identity for a credit card transaction, or a customs agent could verify identity. Moreover, the imager of the present invention can be used as an access device for vehicles. By using an imager, access to a vehicle is linked not to a particular remote control device, but instead to the unique iris patterns of the owner and any number of other authorized users. As described below, the device captures, encodes, and transmits the iris information to a processor and database, preferably stored in the vehicle, which then processes the iris information to verify the user by his iris information. Thus the device itself contains no inherent key, code, or token that controls access. It should be noted that the present invention is not limited to use with automobiles, but can be used with other assets, such as other types of vehicles, boats, residences, and offices. Moreover, one remote access device can be used for multiple assets.

Figure 12:
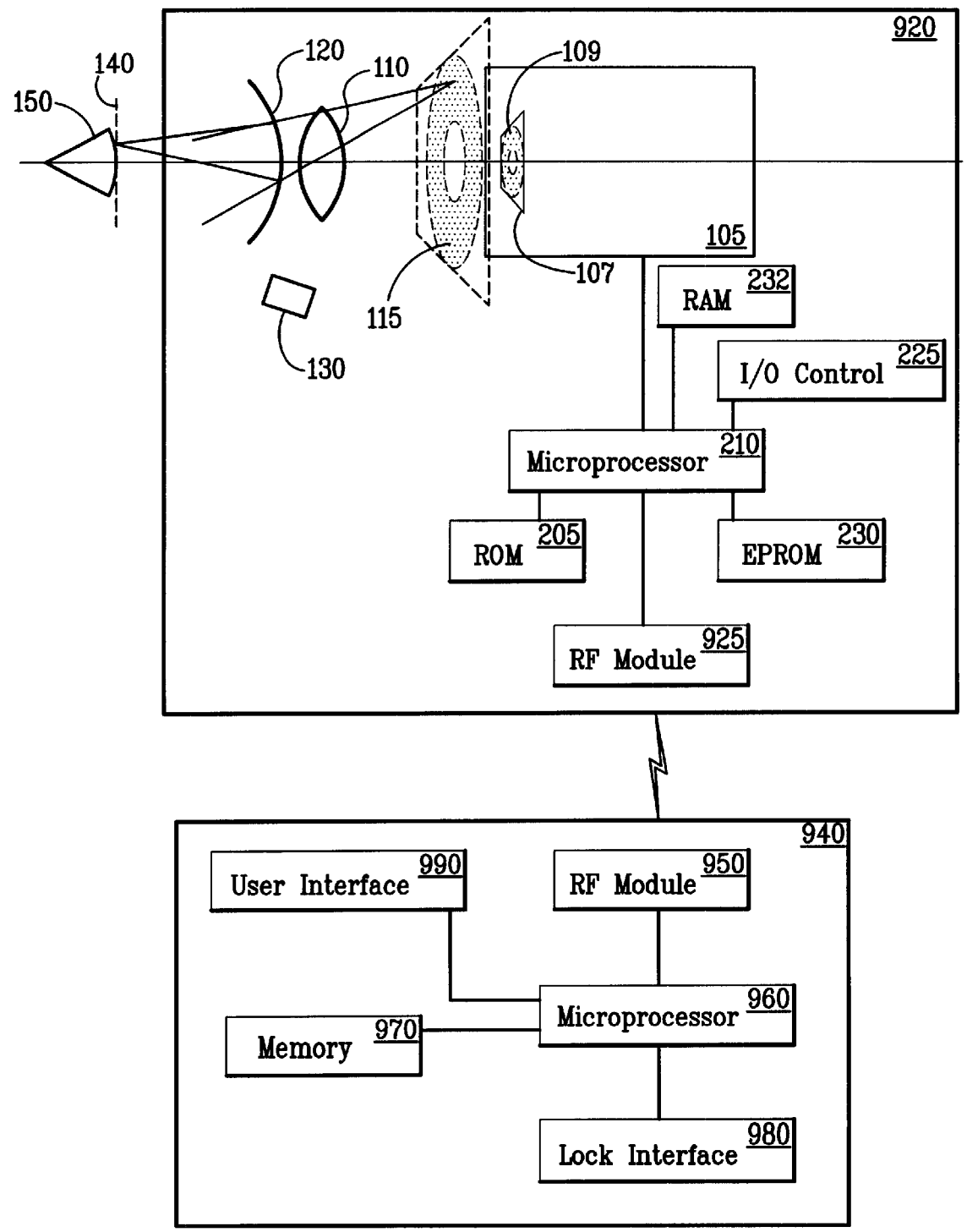
FIG. 12 is a schematic diagram of an imager and a controller system in accordance with the present invention.

An exemplary access device and system in accordance with the present invention is shown in FIG. 12. An imager 920 comprises elements 105–150 that are similar to those described above with respect to FIG. 2A, and their descriptions are not repeated here for brevity. The imager 920 further comprises a microprocessor 210. As described above, the microprocessor 210 performs the processing and encryption of the iris images. The microprocessor 210 runs software held in read only memory (ROM) 205. The processor 210 is connected to the ROM 205, a random access memory (RAM) 232, another memory such as an erasable programmable ROM (EPROM) 230, and an input/output (I/O) controller 225. The RAM 232 is large enough to hold at least one captured image of an iris. The I/O controller 225 is connected to the appropriate circuitry and drivers (not shown) for issuing commands to control the imager 920.

As described above, the image processing consists of a number of image processing steps (such as those described in U.S. Pat. Nos. 5,291,560 and 5,572,596, which are herein incorporated by reference) which lead to extraction of a unique and highly specific digital biometric template (such as an IRISCODE™) that can be used to identify the individual based on intensity patterns within the iris.

In addition to extracting the iris image data and processing it to produce a biometric template, the microprocessor 210 preferably encrypts the template so that the output of the handheld imager 920 is an encrypted biometric template that can be used by a comparison controller system 940 in the vehicle (or other asset) for comparison and user identification. Encryption can be with any of the known encryption techniques using public and private keys to encipher and decipher the data, respectively. The encrypted biometric template from the processor 210 is preferably transmitted via a wireless device, such as an RF module or modem 925 to the comparison controller system 940, although the imager 920 can be hardwired to the system 940.

A receiving device, such as an RF module or modem 950 is disposed within the system 940 and receives the biometric template (which has been optionally encrypted) from the imager 920. A microprocessor 960 decrypts the biometric template, if it has been encrypted, and compares it against other templates or images (or IRISCODEs) stored in a memory (such as a RAM or EPROM) 970 within the system 940. The memory 970 stores selected data representing images of the iris of authorized users. A match of the biometric template with a template stored in the memory 970 identifies the subject whose iris is being imaged. If a user is identified/authenticated, access to the vehicle or asset is granted, and the microprocessor initiates commands to unlock the vehicle via an interface 980. It is contemplated that other commands, such as start ignition or unlock trunk, can also be initiated pursuant to a valid identification.

A user interface 990 is preferably provided in the comparison controller system 940 to indicate status and allow the user to select a recognition mode or an enrollment mode, or delete the entire database if desired. Alternatively, the user interface 990 can be provided in the imager 920. In recognition mode, the processor 960 compares the received biometric template to a database containing the template records of authorized users. In enrollment mode, the processor 960 adds a template record (e.g., the record just received) to the database of authorized users. Any number of template records can be stored; it is limited by the memory in the database. For example, multiple family members might be enrolled in a system used to control access to a car or home. The irises of several business partners might be enrolled in a system used to control access to the company offices. Because the imager 920 itself contains no information that can be used to grant access, it can be stored in any convenient location where it will be accessible to users, though it should be protected from theft and vandalism.

Preferably, the imager 920 is compact, light weight, low cost, and battery-powered. IR LED illumination, CMOS imagers, low power embedded processors, nonvolatile RAM or EEPROM memory, and RF chipsets designed for 900 MHz or 2.4 GHz public use frequency bands can be used. The controller system 940 can rely on external power from the vehicle storage battery or public utilities (in the case, for example, of a residence or office).

The present invention is a powerful security tool because it provides access to a person, and not to a particular key, token, password, PIN number, or other device. In devices according to the present invention, there are security considerations. In many data transmission applications it is important to protect the privacy of the message, assure nonrepudiation, and prevent denial of service. Privacy is not a primary consideration because the iris biometric template data is a pattern of 1s and 0s from which nothing can be learned about the person, and no other personal data is transmitted with it. Nonrepudiation can be automatically assured by iris recognition if a record of vehicle accesses is maintained but this is not usually the intent of such an access control system. Denial of service attacks are an inconvenience and can be overcome through the use of encryption and availability of backup systems (e.g., a conventional key) for emergency situations.

Figure 13:
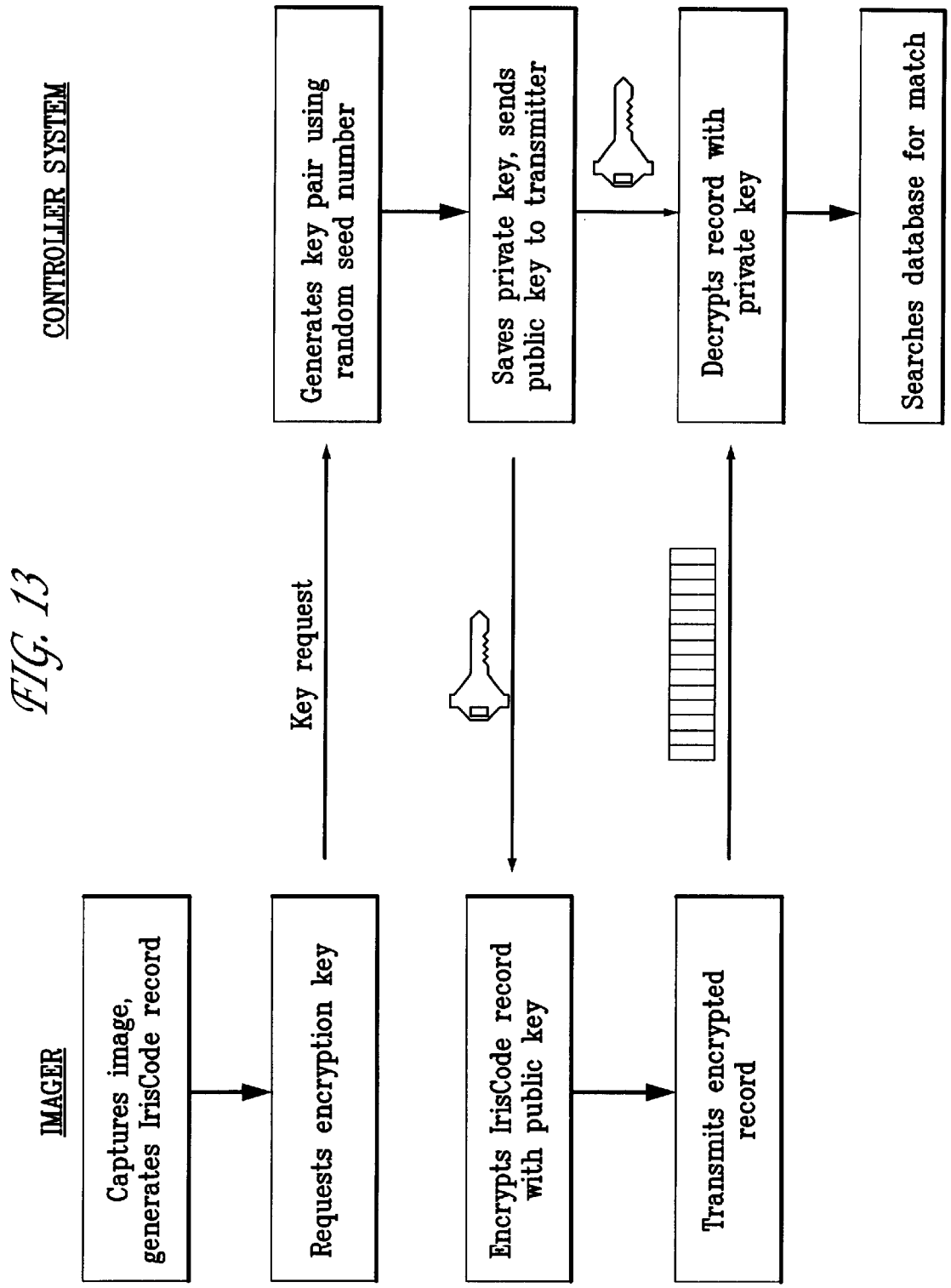
FIG. 13 is a flow diagram of an exemplary method of handshaking and encryption in accordance with the present invention.

One vulnerability is record-and-replay attacks. If the biometric template data were transmitted via RF and recorded during its transmission, the data could conceivably be replayed at a later time to gain access to the vehicle or other asset. Several techniques can be implemented to prevent this. One is to operate synchronized clocks in the transmitter and controller and time-stamp the biometric template data transmitted to the controller. The iris data and time data are hashed and encrypted to prevent tampering, and access is granted only if the received time stamp matches that of the controller. A second approach could use a handshaking technique in which an imager desiring to send data would first request transmission of a public key from the controller system. An exemplary handshaking and encryption technique is shown in FIG. 13. The key would be part of a public-private key pair generated randomly, in response to each request, by the controller system. The public key is sent by the controller system to the imager which uses it to encrypt the data that is transmitted back to the controller system. The controller system then decrypts the code with its private key. Hence, the data generated for a given biometric template record would be different every time it is transmitted and record-and-replay attacks would be foiled.

Although illustrated and described herein with reference to certain specific embodiments, it will be understood by those skilled in the art that the invention is not limited to the embodiments specifically disclosed herein. Those skilled in the art also will appreciate that many other variations of the specific embodiments described herein are intended to be within the scope of the invention as defined by the following claims.

What is claimed is:

1. A system for providing access to a vehicle or other asset, comprising:
   an imager comprising:
      iris acquisition means having a front surface for obtaining an image of an iris of an eye;
      a lens having an image plane disposed in front of the front surface of the iris acquisition means;
      a mirror disposed on a side of the lens opposite the iris acquisition means;
      an illuminator disposed along a side of the mirror;
      a first memory for storing an iris image obtained by the iris acquisition means;
      a processor for extracting a template from the stored iris image; and
      a communications interface for transmitting the template to the controller system; and
   a controller system comprising:
      communications interface for receiving the template from the imager;
      a second memory for storing at least one template of at least one image of an iris of at least one person's eye;
      a processor for comparing the received template with the at least one template in the second memory to identify the person; and
      a lock interface coupled to the processor for receiving a command from the processor responsive to the results of the comparison.

2. The system according to claim 1, wherein the iris acquisition means comprises a camera, and the mirror is a cold mirror.

3. The system according to claim 2, wherein the camera is sensitive to light having a wavelength in a range between about 400 nm and about 1100 nm.

4. The system according to claim 2, wherein the mirror reflects light having a wavelength in a range between about 400 nm and about 700 nm and passes light having a wavelength greater than about 700 nm.

5. The system according to claim 1, further comprising an input device for receiving user input.

6. The system according to claim 1, wherein the illuminator emits light having a wavelength in a range between about 680 nm and about 900 nm towards the iris of the eye being imaged.

7. The system according to claim 1, wherein the processor sends an unlock command via the lock interface to unlock the vehicle or other asset if the comparison indicates a substantial match between the received template and the at least one template stored in the second memory.

8. A method of providing access to a vehicle or other asset responsive to the identification of a person, comprising:
   (a) storing image information of the iris of at least one person's eye in a memory in a controller system;
   (b) illuminating an eye of an unidentified person having an iris with an imager;
   (c) obtaining an image of the iris of the unidentified person;
   (d) determining if the image is an image of sufficient quality for a step (f) of extracting;
   (e) repeating steps (b) through (d) until the image of sufficient quality is obtained;
   (f) extracting an iris template if the image is of sufficient quality;
   (g) transmitting the iris template from the imager to the controller system;
   (h) at the controller system, receiving the iris template from the imager and comparing the iris template with the stored image information to identify the unidentified person; and
   (i) providing access to the vehicle or other asset responsive to a result of the comparing.

9. The method according to claim 8, wherein access to the vehicle or other asset is provided via a lock interface.

10. The method according to claim 8, wherein determining if the image is an image of sufficient quality comprises focus assessment processing the image.

11. The method according to claim 8, wherein vehicle or other asset is unlocked if the comparing identifies the person.

12. The method according to claim 8, wherein providing access to the vehicle or other asset comprises unlocking the vehicle or other asset if the iris template substantially matches the stored image information and wherein the vehicle or other asset remains locked if the iris template does not substantially match the stored image information.

* * * * *